United States Patent [19]

Gordon et al.

[11] 4,452,901

[45] Jun. 5, 1984

[54] ELECTROPHORETICALLY TRANSFERRING ELECTROPHEROGRAMS TO NITROCELLULOSE SHEETS FOR IMMUNO-ASSAYS

[75] Inventors: Julian Gordon; Theophil Staehelin, both of Arlesheim; Harry Towbin, Allschwil, all of Switzerland

[73] Assignee: Ciba-Geigy Corporation, Ardsley, N.Y.

[21] Appl. No.: 261,217

[22] PCT Filed: Mar. 18, 1980

[86] PCT No.: PCT/EP80/00018
   § 371 Date: Apr. 20, 1981
   § 102(e) Date: Apr. 20, 1981

[87] PCT Pub. No.: WO81/02790
   PCT Pub. Date: Oct. 1, 1981

[30] Foreign Application Priority Data

Mar. 20, 1980 [CA] Canada ................................. 348033

[51] Int. Cl.³ .................... G01N 33/54; G01N 33/68; G01N 27/26
[52] U.S. Cl. .................................. 436/506; 204/403; 435/7; 436/516; 436/530
[58] Field of Search ............... 204/180 G, 180 R, 299, 204/403; 436/516, 530, 506; 435/7

[56] References Cited

U.S. PATENT DOCUMENTS

3,554,894 1/1971 Zemel ................................. 204/299

FOREIGN PATENT DOCUMENTS

WO79/00044 2/1979 PCT Int'l Appl. .
1513169 6/1978 United Kingdom .

OTHER PUBLICATIONS

Southern, E. M., (1975), J. Mol. Biol., 98, 503–517.
Broome S., Gilbert W., (1978), Proc. Nat'l. Acad. Sci. U.S.A., 75, 2746–2749.
Sharon, J., Morrison, S. I. & Kabat, E. A., (1979), Proc. Nat'l. Acad. Sci. U.S.A., 76, 1420–1424.
Bowen et al., (Nucleic Acids Research, 8, 1 (1980).
Renart et al,. (Proc. Nat. Acad. Sci. U.S., 76, 3116, 1979).
Arnheim & Souther (Cell 11, 363 (1977)).
Bittner et al., Anal. Biochem. 102, 459–471 (1980).
Kutateladze et al., Anal. Biochem. 100, 129–135 (1979).
Chemical Abstracts, vol. 92, No. 19, issued May 12, 1980, p. 259, Abstract No. 159945h, Anal. Biochem. 1980, 102(2), 459–471.
Chemical Abstract, vol. 92, No. 1, issued Jan. 7, 1980, p. 276, Abstract No. 2752v, Seibutsu Butsuri Kagaku 1979, 22(4), 279–284, Japan.
Analytical Biochemistry, vol. 46, No. 1, issued 1972, pp. 19–32, especially pp. 19, 25–32.
Chemical Abstracts, vol. 73, No. 2, issued Nov. 30, 1970, p. 76, Abstract 111102m, Appl. Polym. Symp. 1969 (publ. 1970), No. 13, 211–233.
Towbin, H. et al., Proc. Nat'l. Acad. Sci. U.S.A., 76, 4350–4354 (Sep. 1979).
Erlich, H. A. et al., Jour. Biol. Chem., 254(23), 12240–12247 (Dec. 1979).
Legocki, R. P. et al., Anal. Biochem., 111, 385–392 (1981).

*Primary Examiner*—Sidney Marantz
*Attorney, Agent, or Firm*—Irving N. Feit

[57] ABSTRACT

Solid supports for proteins consisting of nitrocellulose sheets containing a replica of an electropherogram of proteins as obtained by electrophoretic separation in a gel. Faithful replica of such electropherograms on the nitrocellulose support can be obtained by contacting the gel with a nitrocellulose sheet and applying an electric field perpendicular to the plane of the gel causing an electrophoretic migration of the proteins toward the nitrocellulose sheet where the proteins are adsorbed. Various analytical problems and especially immuno-assays, for enzyme immuno-assays or such involving radioactively labeled indicators, can be made with the new solid supports.

42 Claims, No Drawings

ELECTROPHORETICALLY TRANSFERRING ELECTROPHEROGRAMS TO NITROCELLULOSE SHEETS FOR IMMUNO-ASSAYS

The present invention concerns new solid supports for proteins for analytical purposes, a process for their preparation, and their use, especially as diagnostic tools.

More particularly the invention is directed to porous nitrocellulose sheets containing a replica of an electropherogram of proteins in a gel. The form in which the proteins are immobilized on the nitrocellulose sheet is excellently suitable for analytical purposes, such as the detection and identification of proteins by solid state immuno-assay methods, such as those currently used, for instance radioactive methods, fluorometric methods or enzyme immuno-assays.

The invention thus comprises also the use of the new solid supports for proteins for the immuno detection of proteins, antigens and antibodies, especially as diagnostic tools.

The invention is chiefly based on the finding that it is possible to transfer proteins from a gel (as currently used in protein biochemistry, e.g. a gel used for the electrophoretic separation of proteins) on to sheets of nitrocellulose, that is to say on cellulose nitric acid ester supports in the form of thin sheets, which may contain in addition other cellulose esters, such as cellulose acetate. The transfer of the proteins to the gel can be quantitative, and the immobilized proteins form an exact replica of the pattern which was present in the gel.

Polyacrylamide gel electrophoresis has become a standard tool in every laboratory in which proteins are analyzed and purified. Most frequently, the amount and location of the protein are of interest and staining is then sufficient. However, it may also be important to correlate an activity of a protein with a particular band on the gel. Enzymatic and binding activities can sometimes be detected in situ by letting substrates or ligands diffuse into the gel. In immunoelectrophoresis, the antigen is allowed to diffuse or electrophoretically move against antibody. A precipitate is then formed where the antigen and antibody interact. Modifications have been described in which the antigen is precipitated by directly soaking the separation matrix in antiserum. The choice of electrophoretic systems is then severely limited by the need to have a gel of sufficiently large pore size as to permit the diffusion of the antibody and/or antigen. Such systems are also dependent on concentration and type of antigen or antibody to give a physically immobile aggregate. Attempts have therefore been made to transfer the proteins isolated in gels on to solid supports, as will be described below.

The transfer of the proteins from the gel to the nitrocellulose support is carried out, according to the present invention, by an electric field applied to the gel containing the proteins, causing an electrophoretic migration of the latter, for instance previously separated by some standard electrophoresis procedure, and in the form of an electropherogram. The electric field is applied so that the proteins will migrate in the direction of the nitrocellulose sheet which is in contact with the gel, preferably perpendicular to the plane of the gel. As is explained below, it is surprising that it is possible to obtain a faithful replica of the array of the proteins present in the gel, because spreading of the proteins in the gel under the influence of the inhomogeneous electric field would have been expected, as well as unpredictable complications due to the presence of ionic detergents and because the chemical basis for the binding of the proteins to nitrocellulose is not understood. The immobilized proteins on the nitrocellulose sheet are stable against washing the sheet, for instance against treatment with suitable salt solutions, for instance saline (physiological sodium chloride solution).

If the sheets are to be used for diagnostic purposes or other scientific experiments involving immuno-assays procedures, the sheets shall be treated with appropriate proteins which will satuate the residual adsorption capacities of the nitrocellulose sheet. This is done by saturating the sheet with an individual non-specific protein, or with a mixture of such proteins, or with total serum, or any combination of these ingredients, alone and/or together with the ingredient of the subsequent immuno-assay steps. The only limitation, as described below, is that these should not interfere with or cross-react with any of the specific antibodies in the immuno-assay.

Thus, in the process of the present invention for producing the solid supports for proteins in the form of nitrocellulose sheets containing a replica of an electropherogram of proteins in a gel, this electropherogram is transferred on to a nitrocellulose sheet by contacting the gel with a nitrocellulose sheet and this transfer is achieved by electrophoresis, and, if desired, all residual adsorption capacities of the sheet for proteins are saturated by incubation with an appropriate medium containing proteins capable of being adsorbed by nitrocellulose.

In a preferred form of this process the transfer of the proteins to the nitrocellulose is achieved by electrophoresis perpendicular to the plane of the assembly consisting of the nitrocellulose sheet superposed to the gel.

By the term protein as used in this application there are to be understood proteins as such and also naturally occurring protein conjugates, such as glycoproteins, lipoproteins or protein-nucleic acid complexes.

The transfer of electropherograms from gels to nitrocellulose sheets has already been described in the case of DNA [Southern, E. M. (1975) J. Mol. Biol. 98, 503–517]. However, in this method, immobilization of the gel pattern of DNA onto the nitrocellulose was achieved passively, without electrophoresis. Analysis of protein produced by bacterial colonies on agar plates has been performed by adsorption to antibody coated plastic sheets [Broome S, Gilbert W., (1978), Proc. Natl. Acad. Sci. USA, 75, 2746–2749]. Nitrocellulose sheets have also been used for the adsorption of immunoglobulins selected from hybridoma colonies growing in a gel [Sharon J., Morrison S. I. & Kabat E. A., (1979) Proc. Natl. Acad. Sci. USA, 76, 1420–1424]. Neither of these methods deals with electrophoretically transferred proteins, and, as described, they are not designed to deal with an unlimited number of individual antigen-antibody reactions simultaneously, as the method of the present invention does.

A further method of transfer of proteins from gels to nitrocellulose has been described by Bowen et al [Nucleic acids Research, 8, 1 (1980)]. The transfer is also performed by direct contact of a gel electropherogram with a nitrocellulose sheet. However, in order to obtain the immobilization of the proteins on the nitrocellulose they attempt to first free the proteins of sodium dodecyl sulfate used as detergent in the preceding electrophoresis, by allowing the detergent diffuse out of the gel into a buffer solution. Only in a second step are the proteins allowed to diffuse on to the nitrocellulose. The method is time-consuming and the transfer inefficient (≲10% of the original protein). Renart et al [Proc. Nat. Acad. Sci. U.S. 76, 3116, 17979] use a modified polyacrylamide gel system which can be chemically disrupted in order to increase the rate of transfer also by diffusion of the proteins, as opposed to the electrophoretic system of the present invention. They also used a modified cellulose which has reactive groups attached and covalently binds proteins. This modified cellulose has the disadvantage of needing to be prepared immediately before use, requiring three steps of chemical treatment of the paper and an organic synthesis of a compound which is not readily available. Their procedure is therefore cumbersome to set up in practice.

The electrophoretic transfer of the proteins from the gel to the nitrocellulose sheet according to the present invention is by its simplicity and versatility a decisive step forward in the analysis of proteins. This is because resolution of the original electropherogram is conserved and the recovery of proteins is usually high. Further it is usually difficult to prepare dried polyacrylamide gels for autoradiography because of the tendency to split and crack during drying. The drying of the nitrocellulose sheets is trivial, requiring only a hair dryer or other source of warm air. Because the proteins become concentrated on a very thin layer, autoradiography from $^{14}C-$ and $^{35}-S-$ labeled proteins should be highly efficient even without 2.5-diphenyloxazole impregnation. Tritiaed proteins immobilized on the nitrocellulose sheets can be processed for fluorography by brief soaking in 10% diphenyloxazole in ether.

It is surprising that during the electrophoretic transfer the proteins do not spread out in the gel either by diffusion or as a consequence of the non-uniform electric field applied. The proteins deposit on the nitrocellulose sheet in an exact replica of the position in the original gel. What is especially surprising is that the proteins migrate towards and bind to the nitrocellulose from gels containing detergents, which will affect the properties of individual proteins in a complex and unpredictable manner. In the case e.g. that lauryl sulfate (sodium dodecyl sulfate) is used as denaturant, the proteins are all negatively charged. This would indicate that possibly the proteins remain enveloped by detergent molecules during the electrophoretic transfer. On the other hand, one would expect that the presence of the detergent would prevent the binding of the proteins to the nitrocellulose. This does not happen: the excess detergent is apparently removed either by elecrophoresis or diffusion; or, if it binds to the nitrocellulose, it is in insufficient quantity to interfere with the binding of the proteins; it might also be destroyed if it reaches the electrode. However, if the detergent is destroyed or removed, one might expect that it would also dissociate from the proteins and they would then reverse their sign of the electric charge and migrate in the opposite direction. This does not happen, if, on the other hand, detergent is still associated with the proteins at the moment of their deposition on the nitrocellulose sheet, it is surprising that the protein-detergent complex is adsorbed in very much the same manner as the proteins.

An attempt of using electrophoresis for the transfer of DNA on to nitrocellulose filters has been briefly described by Arnheim & Southern [Cell 11, 363 (1977)]. However, their method is insufficiently well described to set up, and is apparently inferior to the method described earlier by the same authors which relies on diffusion. Although published in 1977 this method has not been widely applied, although their earlier procedure depending on diffusion is extraordinarily widely used. The same authors continue to use their earlier procedure in subsequent publications.

Under the term "nitrocellulose" as referred to the solid supports of the present invention are understood nitric acid esters of cellulose, if desired, in mixture with other cellulose esters. Thus, pure nitrocellulose can be used as consisting of an ester of cellulose having approximately 3 nitric groups per 6 C atoms. Alternatively, nitric acid esters with less than such number of groups can be used. When mixed esters of nitric acid and other acids are used, these latter can be any acids normally used for making cellulose esters, preferably aliphatic acids having from 1 to 7 C atoms, such as acetic acid, propionic acid, the butyric or valerianic acids. It is preferable to use a "nitrocellulose" known in commerce under the name of "Millipore" (commercialized by the firm Millipore, Bedford, Mass. USA) having a pore size of 0.45 micron, and which represents a mixed ester of nitric acid and cellulose acetate. The pore size of the cellulose esters to be used may vary within wide limits, preferably between a size of 0.025 and 14 micron.

The sheets may have dimensions typically of 12×14 cm, corresponding to the most commonly used slab gel electrophoresis system [Howard, G. A. & Traut, R. R., 1973, FEBS Letters 29, 177-180], but may range from, for example, the micro system (50×75 mm) using microscope slides [Linz, A., Collatz E. O., Wool, I. G., Molec. gen. Genet (1976), 144, 1-9] to the original macro (20×20 cm) system [Kaltschmid, E., Wittmann, H. G. (1970), Proc. Nat. Acad. Sci. US 67, 1276-1280]. The gel slab thickness can range preferably from 0.8 to 5 mm.

The electropherograms to be transferred to the nitrocellulose sheets may have been obtained in various gel media, such as agarose, agar, and especially polyacrylamide. Usually the electrophoretic separation of proteins in a gel is performed in the presence of protein denaturing agents, such as, e.g. anionic detergents, especially esters of higher aliphatic alcohols having between 8 and 20 C atoms, primarily with sodium dodecyl sulfate. As a protein denaturing agent there is also especially used urea. In the electrophoretic transfer of proteins according to the process of the invention the nature of the individual proteins denaturing agent and buffer used in the transfer determines the direction of the electric field to be applied in the electrophoresis. In the presence of the sodium dodecyl sulfate, the proteins will always migrate toward the anode. At any rate, the migration direction of the proteins in a given substrate can be determined by placing nitrocellulose sheets on both sides of the gel electropherogram.

The electropherograms obtained in the gel slabs commonly used in the electrophoretic separation of proteins may be one dimensional or two dimensional, as obtained by known techniques. The transfer of the electropherograms on to the nitrocellulose sheets can be made according to any suitable technique which uses in principle an electrophoretic chamber in which the gel slab is introduced, containing a suitable medium, and the nitrocellulose sheet is applied on that side of the slab where the proteins will migrate. A preferred assembly for such transfer consists of: a scouring pad known as Scotch Brite 96 (3M) which is supported by a stiff plastic grid (disposable micropipette tray, Medical Laboratory, Inc., New York); a second pad and plastic grid, opposed to the first, contains the gel slab with the nitrocellulose sheet kept evenly and firmly pressed on it by rubber bands strung around both pads.

For electrophoresis gels run in the absence of detergent on the presence of non-ionic detergents, the transfer medium shall be dilute acid to ensure that the pH is below the isoelectric points of all proteins. For example, dilute acetic acid is usually used. The proteins will then migrate toward the cathode. For protein complexed with an anionic detergent a slightly alkaline pH of about 7.5- to about 10 is appropriate to maintain the detergent protein complexes and the anodal migration. A pH of about 8.5 is optimal e.g. when dodecyl sulfate is used as detergent.

The sheets of nitrocellulose containing the exact replica of the electropherogram in the gel may be used, inter alia, for various types of immuno assays. The present invention thus comprises also the use of the solid supports in the form of the nitrocellulose sheets containing the immobilized proteins for the immuno detection of proteins, antigens and antibodies, and the solid nitrocellulose supports therefore represent new diagnostics tools. The proteins transferred on to the nitrocellulose sheet may be from any source: animals, plants, bacteria, viruses, and may be any known naturally occurring protein conjugates such as glycoproteins and lipoproteins, and may also be protein-nucleic acid complexes such as ribosomes or nuclear ribonucleoprotein complexes. Among the class of viral and bacterial proteins are pathogens and animal proteins and protein complexes causing auto-immune disease.

If desired, proteins can be located in the sheets by a staining procedure. The proteins can be strained on the nitrocellulose sheet, for instance using amido black, and excess stain removed, for instance using methanol/acetic acid/water.

For the use in immuno assays procedures, the residual binding capacities of the nitrocellulose sheets have to be saturated by treatment with one or more types of proteins different from those immobilized and not cross-reacting with any of the antibodies subsequently used. This can be achieved directly after the transfer has been made. In a preliminary step the residual binding sites of the nitrocellulose sheet are saturated by treatment with non-specific proteins, for instance bovine serum albumin. Such proteins are advantageously diluted in physiological saline, and the nitrocellulose sheet is incubated with this solution, preferably at slightly elevated temperature, for instance between about 30° and 50°, preferably at about 40°, and washed with physiological saline. After this preliminary treatment there may still be present protein binding sites which have not yet been completely blocked, which have also to be blocked when immuno assays have to be carried out. If there is background adsorption due to remaining binding sites or exchange of the non-specific protein, it can be prevented by carrying out the incubation with the first antiserum and that with the indicator antibody in the continued presence of the same non-specific protein and additionally in the presence of total serum, as carrier, derived from the same or related species to that from which the indicator antibody is derived. The continued presence of these mixtures of proteins both blocks remaining binding sites, and tends to prevent, by competition, exchange of the antibodies with proteins previously bound to non-specific sites. The carrier serum thus used should not be from a species which contains immunoglobulins which cross react with the indicator antibody. The preferred conditions for carrying out these steps are with concentrations of 3% (weight/volume) of bovine serum albumin as non-specific protein and 10% (volume/volume) of the carrier serum, all diluted in physiological saline. Alternatively, the treatments with the non-specific protein and serum used as carrier might be carried out separately rather than in combination with the treatments with anti-serum and indicator antibody. The immuno assay with the antiserum to be analyzed can be made by incubation with such serum diluted according to the expected antibody concentration, usually in the range of 1:10 to 1:1000 in physiological saline, for instance in the range of 2 hours to overnight, at room temperature, and then washed extensively with physiological saline. The indicator antibody is radioactively labeled, or conjugated with a fluorescent substance, or with an enzyme capable of giving a color reaction with its substrate. The indicator antibody is usually diluted about 50-fold in a mixture of the above named first non-specific protein and the carrier serum, incubated 30 minutes, and washed again in physiological saline.

These methods are carried out according to techniques known per se and using known indicators. Thus, e.g. $^{125}$I-labeled immunoglobulin can be used in autoradiography, immunoglobulin conjugated with fluorescein for the fluorometric method or with horseradish peroxidase for the enzyme immune method, with the use of o-dianisidine in the presence of hydrogen peroxide, as the substrate for the peroxidase for eliciting a color reaction, in the case of the horseradish peroxidase method, with the colored reaction product being insoluble and remaining immobilized at the site of formation.

By these immuno assays methods it is possible, by using known proteins transferred to the nitrocellulose support, to identify unknown pathological antibodies in a serum, for instance an animal serum or human serum. Conversely, by using known antibodies in a serum, and known proteins immobilized by the method of the present invention on the nitrocellulose sheet, the presence of such proteins in solution in an unknown sample can be determined by its ability to compete with the antibody reaction on the solid support, by well known procedures. In the first instance the known proteins, for instance transferred from a one dimensional electropherogram in a gel, can also be separated by cutting the sheet into various strips corresponding to each isolated protein, or parallel replica strips containing all separated proteins, and with such strips various individual sera containing unknown antibodies can be easily screened.

With all the indicated antibodies described the method is very sensitive, and small amounts of electrophoretically separated antigen, as well as small amounts of antibody in a serum of low titer, can be detected. The peroxidase procedure has the additional merit of simplicity and permitting direct visualization with no special instrumentation. Because the antigen is immobilized on a sheet, the antibody is not required to form a precipitate with the antigen. The blotting technique therefore has the potential for immunoelectrophoretic analysis of proteins by using binding of monovalent immunoglobulin fragments or binding of antibodies directed against a single determinant, such as monoclonal antibodies produced by hybridomas. This could not be done by current immunoelectrophoretic techniques. If hybridoma clones are obtained from a mouse immunized with impure immunogen, it is possible to use the technique to screen for clones making antibody directed against a desired antigen. Provided the desired antigen has a characteristic mobility in polyacrylamide gel electrophoresis the appropriate clone can be selected without ever having pure antigen.

The procedure of immuno assays according to the present invention also has a potential as a tool for screening pathological sera containing auto-antibodies—e.g. those against ribosomes or other nucleoprotein complexes. The precise identification of the immunogenic components may be a useful diagnostic tool for various pathological conditions.

A further advantage of immobilization of proteins on nitrocellulose is the ease of processing for autoradiography. Conventional staining, destaining, and drying of polyacrylamide gels takes many hours, and the exact drying conditions are extremely critical, especially for 18% gels as used in the second dimension for ribosomal proteins. When the proteins are transferred to a nitrocellulose support, as described here, the electrophoretic blotting takes 1 hour, staining and destaining less than 10 minutes, and drying an additional 5 minutes. This is thus both faster and simpler than conventional procedures, and it eliminates the tedious and hazardous procedure of soaking the gels in diphenyloxazole.

The technique is applicable to any analytical procedure depending on formation of a protein ligand complex. With the blotting technique, the usual procedure of forming a complex in solution and retaining it on a membrane would have to be reversed: the protein, already adsorbed to the membrane, would have to retain the ligand from a solution into which the membrane is immersed. Interactions that can possibly be analyzed in this way include hormone-receptor, cyclic AMP-receptor, and protein-nucleic acid interactions. The ligand may also be a protein. Enzymes separated on polyacrylamide gels could also be conveniently localized on blots by in situ assays. A critical requirement for these applications is that the protein is not damaged by the adsorption process and that binding sites remain accessible to ligands and substrates. In this respect, considerations similar to those in affinity chromatography and insoluble enzyme techniques pertain.

The method can also be adapted to the procedure for the analysis of proteins eluted from bands in polyacrylamide gels by one-dimensional fingerprints [Cleveland et al (1977), J. Biol. Chem. 252, 1102–1106]: one could label by iodination in situ on the nitrocellulose, and then carry out the proteolytic digestion.

The following Examples illustrate the invention. The temperatures are indicated in degrees centigrades.

EXAMPLE 1

*Escherichia coli* ribosomal L7 and L12 are extracted by the method described in "Hamel, E., Koka, M. & Nakamoto, T. (1972) Biol. Chem. 247, 805–814" from 50S ribosomal subunits and purified as described in "Möller, W., Groene, A., Terhorst, C. & Amons, R. (1972) Eur. J. Biochem. 25, 5–12" by ion-exchange chromatography on carboxymethyl- and DEAE-cellulose. Antibodies are raised in a goat by injecting 250 $\mu$g of protein emulsified with complete Freund's adjuvant intracutaneously distributed over several sites. Bacillus pertussis vaccine (1,5 ml) of Bordet-Gengou vaccine (Schweizerisches Serum- und Impfinstitut, Bern, Switzerland) is given subcutaneously with every antigen injection. Booster injections of the same formulation are given on days 38, 79 and 110. The animal is bled on day 117 and the antiserum to be analyzed is taken from the jugular vein.

A mixture of *Escherichia coli* total ribosomal proteins is subjected to electrophoresis in two dimensions as follows:

The first dimension gels are cast in glass tubes (inside diameter, 2.4 mm) with the acidic and basic proteins run in separate gels with opposite polarity. The separating gel (8 M urea; 8% acrylamide; 0.021 M EDTA; 0.5 M boric acid; 0.4 M Tris; 0.3% N,N,N', N'-tetramethylethylenediamine, 0.3% N,N'-methylenebisacrylamide, pH 8.6; 3 $\mu$l/ml of gel solution of 10% ammonium persulfate) with migration in the direction of the anode has a length of 5 cm and the gel with migration towards the cathode a length of 7.5 cm. A 5-mm stacking gel (8 M urea; 4% acrylamide; 0.2%, N,N'-methylenebisacrylamide; 0.002 M EDTA; 0.005 M boric acid; 0.06% N,N,N',N'-tetramethylethylenediamine, pH 8.6; 20 $\mu$l/ml of gel solution of 0.5 mg/ml of riboflavin, 5 mg/mm of ammonium persulfate) is layered on top of the separating gel. In some cases, the length of the gel is increased to 10 cm in order to visualize possible faster migrating proteins. (None are found.) The lower electrode buffer is 0.0064 M EDTA; 0.155 M boric acid; 0.12 M Tris; pH is adjusted to 8.6 with 10 M NaOH. Prior to use the gel tubes are coated with 1% v/v dimethyldichlorosilane in toluene and allowed to dry at room temperature. The sample of c. 100 $\mu$g of total *E.coli* ribosomal protein is dissolved in 40 $\mu$l to 50 $\mu$l of sample buffer (8 M urea; 0.002 M Na.EDTA; 0.005 M boric acid; 0.06% N,N,N',N'-tetramethylethylenediamine; 0.04% 2-mercaptoethanol; pH 8.6), with 5 $\mu$l of 0.05% bromphenol blue (acidic proteins) or 0.1% pyronin G (basic proteins) in 20% glycerol added as tracking dye and heated to 40° for 20 minutes. After cooling to room temperature, the sample solution is layered on to the stacking gel and carefully overlayered with reservoir buffer. Stacking is 100 V for 15 minutes, and electrophoresis in the direction of the anode is continued at 175 V, and towards the cathode at 275 V for a total of 5 hours. Gels are removed from the tubes with a fine needle and syringe by gently injecting 10% glycerol between the gel and tube wall. After removal, the gels are soaked in 0.3 N HCl for 5 minutes and placed into second-dimension gel solution for 10 minutes.

The second-dimensional gel is as described by Howard, G. A. & Traut, R. R. (1973), FEBS LETTERS 29, 177–180, except that the amount of N,N'-ethylenebisacrylamide is 0.38% w/v. Electrophoresis is at a constant 105 V for 14 hours. The dimensions of the slab are 11×14 cm and it is 2 mm thick.

The proteins are then transferred to the nitrocellulose sheets as described in the general part, using Millipore sheets in roll form of pore size 0.45 $\mu$m. The sheet is briefly wetted with water and put on the pad as described. The gel used for electrophoresis is put on the nitrocellulose sheet and care is taken to remove all air bubbles. The second pad and plastic grid are added and rubber bands are strung around all layers. The gel is thus firmly and evenly pressed against the nitrocellulose sheet. The assembly is put into an electrophoretic destaining chamber with the nitrocellulose sheet facing the cathode. The chamber contains 0.7% acetic acid. A voltage gradient of 6 V/cm is applied for one hour. The transfer of proteins to the nitrocellulose is quantitative as evidenced by lack of detectable protein in the original gel.

The electrophoretic blots are soaked in 3% bovine serum albumin in physiological saline (0.9% NaCl/10 mM Tris-HCl, pH 7.4) for one hour at 40° C. to saturate additional protein binding sites. They are rinsed in saline and incubated with 5 ml of the following: the goat antiserum obtained above having a titer of 340 pmol of 70S ribosomes per ml of serum, as determined by turbidity formation [Howard G., Smith R. L., Gordon J. (1976), J. Mol. Biol. 106, 623–637], diluted in a ratio of 1:10 in saline containing 3% bovine serum albumin and 10% rabbit carrier serum. The sheets are washed in saline (about five changes during 30 minutes, total) and incubated with the second (indicator) antibody directed against the immunoglobulins of the first antiserum.

Horseradish peroxidase-conjugated rabbit anti-goat immunoglobulin G (Nordic Laboratories, Tillburg, Netherlands) are reconstituted before use according to the manufacture's instructions.

Horseradish peroxidase-conjugated immunoglobulins preparations are used at 1:2000 dilution in saline containing 3% bovine serum albumin and 10% rabbit serum. The blots are incubated for 2 hours at room temperature and washed as described above. For the color reaction [based on Avrameas, S. & Guilbert, B. (1971) Eur. J. Immunol. I, 394–396] the blots are soaked in a solution of 25 $\mu$g of o-dianisidine per ml/0.01% $H_2O_2$/10 mM Tris-HCl, pH 7.4. This is prepared freshly from stock solutions of 1% o-dianisidine in methanol and 0.30% $H_2O_2$. The reaction is terminated after 20–30 minutes by washing with water. The blots are dried between filter paper. Drying considerably reduces the background staining. The blots are stored protected from light.

The spots of the cross reacting proteins L7 and L12 can then be readily identified in the two dimensional pattern.

EXAMPLE 2

The purified proteins L17/L12 as described in Example 1 are separated by electrophoresis in a gel, corresponding to the second dimension only, of Example 1. The same detection procedure is also used with peroxidase-conjugated rabbit anti-goat immunoglobulin. The amount of protein applied to 1 cm slots in the top of the gel is varied over a wide range. In general, the bands of protein are sharper after only one dimension of electrophoresis, so that the sensitivity of detection is corresondingly higher. There is a significant color reaction with as little as 50 pg of the proteins L7/L12.

EXAMPLE 3

Chicken liver ribosomal subunits are prepared and separated, and the total protein prepared from them, as already described in detail. [Ramjoué, H. P. R. & Gordon, J. (1977), J.Biol.Chem. 252, 9065–9070]. They are tritiated by reductive methylation with formaldehyde and sodium bortritiide [Moore, G. & Crichton, R. R. (1974), Biochem. J. 143, 604–612]. The radioactive protein is diluted with a suitable amount of nonradioactive carrier protein of the same kind, and 35 $\mu$g is applied to duplicate identical gels. They are subjected to two dimensional electrophoresis as described in Example 1. One gel is stained directly for 4 hours with Coomassie blue R250 (0.1% in 7.5% acetic acid and 50% methanol) and destained electrophoretically in 7.5% acetic acid, 7.5% methanol. The other gel is transferred electrophoretically to nitrocellulose as described in Example 1, stained with amido black for 3 minutes (0.1% in 45% methanol, 10% acetic acid) and destained with 90% methanol, 2% acetic acid. Individual stained spots are cut out and radioactivity determined after combustion in a sample oxidizer (Oxymat, Intertechnique, France) as $^3H_2O$. The efficiency of transfer is calculated as the ratio of the radioactivity in a spot in the nitrocellulose sheet to that in the corresponding spot in the duplicate gel. The mean efficiency of transfer is $(108\pm20)\%$ for this group of proteins. This is completely quantitative and the standard deviation indicated is within the confidence limits with which one can cut individual spots.

EXAMPLE 4

Subunits from chick liver ribosomes are prepared as in Example 3, combined in equimolar amounts and used to elicit antibodies in a series of individual mice. Each (BALB/C strain) mouse receives 200 $\mu$g of the preparation emulsified in 125 $\mu$g of Freund's Complete Adjuvant, and injected in one intraperitoneal and four subcutaneous sites. Booster injections of 400 $\mu$g of ribosomes in physiological saline are given intraperitoneally on days 33, 57, 58, 59. The animals are bled by tail incision on day 71. The individual mouse sera are examined for their contents of antibodies against individual ribosomal proteins as follows. Total chick liver ribosomal protein prepared as above (400 $\mu$g) is applied as a 14 cm line to the top of a gel slab corresponding to the second dimension of the electrophoresis of Example 1. The electropherogram is transferred to a nitrocellulose sheet as in Example 1, and treated with bovine serum albumin in saline in the same way. The sheet is then cut into 5 mm wide strips parallel to the direction of electrophoresis. Each strip then contains a representative section of the entire original electropherogram. The individual mouse sera are then diluted 50-fold into physiological saline containing 3% bovine serum albumin and 10% non-immune goat serum. Each strip of nitrocellulose is incubated for 6 hours at room temperature in 250 $\mu$l of this dilution, and washed in physiological saline as in the first Example.

The second indicator antibody is prepared as follows: hyperimmune sheep anti mouse immunoglobulin is purified by affinity chromatography on Sepaharose-bound mouse myeloma proteins containing $\alpha$, $\mu$, $\gamma_1$, $\gamma_{2A}$, $\gamma_{2B}$, $\kappa$ and $\lambda$ chains. The iodination is carried out by the chloramine T method [Matsku, I. & Zöller, M. (1977), Immunochemistry 14, 367–371] using 450 $\mu$g of protein and 1.5 mCi of $Na^{125}I$ in 0.5 ml for 60 seconds at room temperature. The reaction is stopped with excess sodium metabisulfite and non-radioactive NaI to a final concentration of 10 mM. The excess free iodide is removed on a Sephadex G25 column previously saturated with physiological saline and 0.1% bovine serum albumin. The labeled antibody is stored in 0.75% bovine serum albumin. The specific activity is c. 1.5 $\mu$Ci/$\mu$g. This is diluted into physiological saline containing 3% bovine serum albumin and 10% normal goat serum, to $10^6$ cpm/ml. The nitrocellulose strips are incubated in 250 $\mu$l of this solution for 6 hours at room temperature, washed with 5 changes of physiological saline over 0.5 hours, dried with a hair dryer, and exposed to Kodak X-Omat R film for 6 days. The autoradiogram shows the heterogeneity of the response of the individual mice to a complex set of immunogens. This procedure is a prototype for the screening of individual sera for the presence of individual antibodies against a complex set of immunogens.

EXAMPLE 5

Human serum (1 μl) is subject to electrophoresis in one dimension according to the widely used method [Laemmli, U.K. (1970), Nature 227, 680–685] with a 15% acrylamide gel. The electrophoretic transfer from the gel to a nitrocellulose sheet is in a medium containing 25 mM Tris, 192 mM glycine, 20% methanol, pH 8.3, and the sheet is on the anodal side of the gel. The position of the human immunoglobulin G in the nitrocellulose sheet is located as performed in the last step of Example 1, except tht peroxidase conjugated rabbit anti-human IgG is used. The result shows a band of stain corresponding to the position to be expected from the molecular weight of the IgG fraction in the original electropherogram. This shows that the dodecyl sulfate complex of this protein is successfully transferred to the nitrocellulose sheet, and is also still capable of binding its respective antibody. Other similar examples show that with a wide variety of proteins that essentially all get transferred from such gels containing sodium dodecyl sulfate, without loss of resolution or antigenicity, although the efficiency of transfer is not systematically as high as that for gels not containing detergent, such as in Example 3.

What we claim:

1. A solid support for proteins consisting of a porous nitrocellulose sheet containing a replica of an electropherogram of proteins in a gel wherein the replica is obtained by electrophoretic transfer of said electropherogram from the gel.

2. The solid support as claimed in claim 1, wherein the electropherogram is one-dimensional.

3. The solid support as claimed in claim 1, wherein the electropherogram is two-dimensional.

4. The solid support as claimed in claim 1, wherein the nitrocellulose sheet contains a replica of an electropherogram in a polyacrylamide gel.

5. The solid support as claimed in claim 1, wherein the nitrocellulose sheet contains a replica of an electropherogram in agar, agarose, or in starch.

6. The solid support as claimed in claim 1, wherein nitrocellulose is present in admixture with an other cellulose ester.

7. The solid support as claimed in claim 1, wherein nitrocellulose is present in admixture with cellulose acetate.

8. The solid support as claimed in claim 1, wherein nitrocellulose is a nitric acid ester of cellulose containing about 3 nitric acid groups per 6 C atoms.

9. The solid support as claimed in claim 1 wherein nitrocellulose is a nitric acid ester of cellulose with less than 3 nitric acid groups per 6 C atoms.

10. The solid support as claimed in claim 1, wherein said replica is derived from animals, plants, bacteria or viruses.

11. The solid support as claimed in claim 1, wherein said proteins are known naturally occurring protein conjugates.

12. The solid support as claimed in claim 1, wherein said proteins are glycoproteins or lipoproteins.

13. The solid support as claimed in claim 1 wherein said proteins are protein-nucleic acid complexes.

14. The solid support as claimed in claim 1 wherein said proteins are protein complexes causing autoimmune diseases.

15. The solid support as claimed in claim 1, wherein the pore size of the nitrocellulose sheet is in the range of 0.025 μm and 14 μm.

16. The solid support as claimed in claim 1 wherein the pore size of the nitrocellulose sheet is of about 0.4–0.5 μm.

17. The solid support as claimed in claim 1, wherein nitrocellulose is present in admixture with cellulose acetate and wherein the pore size of the sheet is 0.45 μm.

18. The solid support as claimed in claim 1 wherein all residual adsorption capacities for proteins have been saturated by incubation with appropriate media containing proteins capable of being adsorbed by nitrocellulose.

19. A process for obtaining a solid support for protein consisting of a porous nitrocellulose sheet containing a replica of an electropherogram of proteins in a gel, comprising transferring the electropherogram from the gel to the nitrocellulose sheet by electrophoresis.

20. The process as claimed in claim 19, wherein the electropherogram is transferred from a gel slab also containing a protein denaturing agent, the electrophoretic transfer being effected by applying an electric field perpendicular to the plane of the gel slab, the nitrocellulose sheet facing the electrode toward which the proteins will migrate.

21. The process as claimed in claim 19, wherein the gel is a polyacrylamide gel.

22. The process as claimed in claim 19, wherein the gel slab is an agar, agarose, or starch gel slab.

23. The process as claimed in claim 19, wherein the nitrocellulose sheet is pressed against the gel slab in between two pads kept tightly together by elastic bands, and this assembly is put into an electrophoretic chamber containing an acidic or alkaline medium or a buffer.

24. The process as claimed in claim 19, wherein the gel slab also contains an anionic detergent as protein denaturing agent and the electrophoretic transfer is made in the presence of a buffer in the range of pH 7.5–10.

25. The process as claimed in claim 19, wherein the gel slab also contains a non-ionic detergent as protein denaturing agent and the electrophoretic transfer is made in the presence of dilute acid.

26. The process as claimed in claim 19, wherein the gel slab also contains sodium dodecyl sulfate or urea as protein denaturing agent.

27. The process as claimed in claim 19, wherein all residual adsorption capacities of the nitrocellulose sheet for proteins are saturated by incubation with an appropriate medium containing proteins capable of being absorbed by the nitrocellulose.

28. The process as claimed in claim 19, wherein the nitrocellulose sheet containing the immobilized proteins is contacted with non-specific proteins in physiological saline at slightly elevated temperature, to saturate further adsorption binding sites.

29. The process as claimed in claim 28, wherein the nitrocellulose sheet containing the immobilized proteins is incubated for about one hour at about 40° C. in physiological saline.

30. An immunoassay for the identification or detection of proteins or their respective antibodies comprising:

separating the proteins by electrophoresis in a gel, electrophoretically transferring the electropherogram to a porous nitrocellulose sheet, and contacting the nitrocellulose sheet with an antiserum containing known antibodies; or contacting a serum containing said respective antibodies with a porous nitrocellulose sheet containing a replica of an electropherogram of known proteins in a gel wherein the replica is obtained by electrophoretic transfer of said electropherogram from the gel.

31. The immunoassay as claimed in claim 30 wherein the proteins immobilized on the nitrocellulose sheet are known and a pathological antibody is detected.

32. The immunoassay as claimed in claim 30 for the detection of unknown proteins on the nitrocellulose sheet by using known antibodies.

33. The immunoassay as claimed in claim 30 for the detection of antibodies contained in different sera, wherein the nitrocellulose sheet containing individual specific known proteins previously separated electrophoretically in one or two dimensions and transferred to the nitrocellulose support is cut into strips representing sections of the same electropherogram and the strips are contacted with said sera.

34. The immunoassay as claimed in claim 30, wherein all sera or proteins are diluted in physiological saline.

35. The immunoassay as claimed in claim 30, using known antigens revealed with known antibodies and using this combination to detect the presence of unknown antigens by competition.

36. The immunoassay as claimed in claim 30, wherein the nitrocellulose sheet is incubated with the antiserum to be analyzed in the presence of non-specific proteins also capable of saturating any residual adsorption sites, and proteins contained in a carrier serum derived from the animal from which the indicator-antibody is also derived or from a closely related animal species.

37. The immunoassay as claimed in claim 36 wherein the nitrocellulose sheet is treated with a non-specific protein to saturate residual adsorption capacities prior to incubating with the antiserum to be analyzed.

38. The immunoassay as claimed in claim 30, wherein the nitrocellulose sheet is finally washed in saline and incubated with the indicator antibody.

39. The immunoassay as claimed in claim 38, wherein the nitrocellulose sheet is finally washed in saline, incubated with the indicator antibody which is radioactively labeled, and the detection is carried out by autoradiography.

40. The immunoassay as claimed in claim 38, wherein the indicator antibody is conjugated with a fluorescent indicator and the detection is carried out fluorometrically.

41. The immunoassay as claimed in claim 38, wherein the indicator antibody is conjugated with an enzyme capable of giving a color reaction with a suitable substrate and the detection is carried out colorimetrically or visually.

42. The immunoassay as claimed in claim 41, wherein horseradish peroxidase conjugated with immunoglobulin is used as enzyme and o-dianisidine in diluted hydrogen peroxide is used as substrate.

* * * * *